(12) United States Patent
Perone

(10) Patent No.: US 7,291,156 B1
(45) Date of Patent: Nov. 6, 2007

(54) OBSTETRICAL VACUUM EXTRACTOR WITH A PULL-SENSING HANDLE GRIP

(76) Inventor: Nicola Perone, 8827 Memorial Dr., Houston, TX (US) 77024

(*) Notice: Subject to any disclaimer, the term of this patent is extended or adjusted under 35 U.S.C. 154(b) by 500 days.

(21) Appl. No.: 10/615,566

(22) Filed: Jul. 8, 2003

Related U.S. Application Data

(63) Continuation-in-part of application No. 10/460,830, filed on Jun. 12, 2003, now Pat. No. 7,163,544, which is a continuation-in-part of application No. 10/455,910, filed on Jun. 6, 2003, now Pat. No. 7,014,642.

(51) Int. Cl.
*A61B 17/42* (2006.01)
(52) U.S. Cl. .................................................. 606/122
(58) Field of Classification Search ............... 606/119, 606/120, 121, 122, 123, 124, 127, 42, 48, 606/50, 51, 52
See application file for complete search history.

(56) References Cited

U.S. PATENT DOCUMENTS 3,785,381 A * 1/1974 Lower et al. ............... 606/122
6,468,284 B1 * 10/2002 Wallace ...................... 606/123

OTHER PUBLICATIONS

Moolgaoker, A.S., Ahamed, S.O.S., Payne, P.R. A comparison of different methods of instrumental delivery based on electronic measurement of compression and traction. Obstet. Gynecol. 1979; 54:299-309.
Mishell, D., Kelly, J.V. The obstetrical forceps and the vacuum extractor: an assessment of their compressive force. Obstet. Gynecol. 1962; 19:204-6.
Duchon, M.A., De Mund, M.A., Brown, R.H. Laboratory comparison of modern vacuum extractors. Obstet. Gynecol. 1988; 71:155-8.
Hofmeyer, G.J., Gobetz, L., Sonnendecker, E.W.W., and Turner, M.J. New design rigid and soft vacuum extractor cups: a preliminary comparison of traction forces. Br. J. Obstet. Gynaecol. 1990; 97: 681-685.
Center for Devices and Radiological Health. FDA Public Health Advisory: Need for caution when using vacuum assisted delivery devices. May 21, 1998.
Plauche, W.C. Fetal cranial injuries related to delivery with Malmstrom vacuum extractor. Obstet. Gynecol. 1979; 53: 750-7.
Vacca, A.: Operative vaginal delivery: clinical appraisal of a new vacuum extraction device. Aust NZ J. Obstet. Gynaecol. 2001; 41:2:156-160.

* cited by examiner

*Primary Examiner*—Kevin T. Truong
(74) *Attorney, Agent, or Firm*—Raymond R. Ferrera

(57) ABSTRACT

The invention consists of a new obstetrical vacuum extractor which includes a bell-shaped fetal contact cup made of flexible material, with a hollow and substantially rigid stem, a pull-sensing handle grip attached to the end of the stem, and a tube connected with one end to the cup stem and with the other to a vacuum source. The pull-sensing grip contains electronic hardware whose purpose is to reduce the risk of fetal trauma caused by frequent cup detachment ("pop-off") and excessive traction force, during a vacuum-assisted delivery. The hardware includes a strain gauge to measure the traction force applied to the vacuum extractor during a delivery, a speaker to alert the doctor when the traction force approaches a level sufficient to cause a fetal cup "pop-off", and a transceiver for the wireless transmission of the traction data to a receiver connected to a lap-top computer, which generates a graphic representation of such data, and emits a warning signal when pre-set time limit of continuous cup application on the fetal scalp is reached.

18 Claims, 5 Drawing Sheets

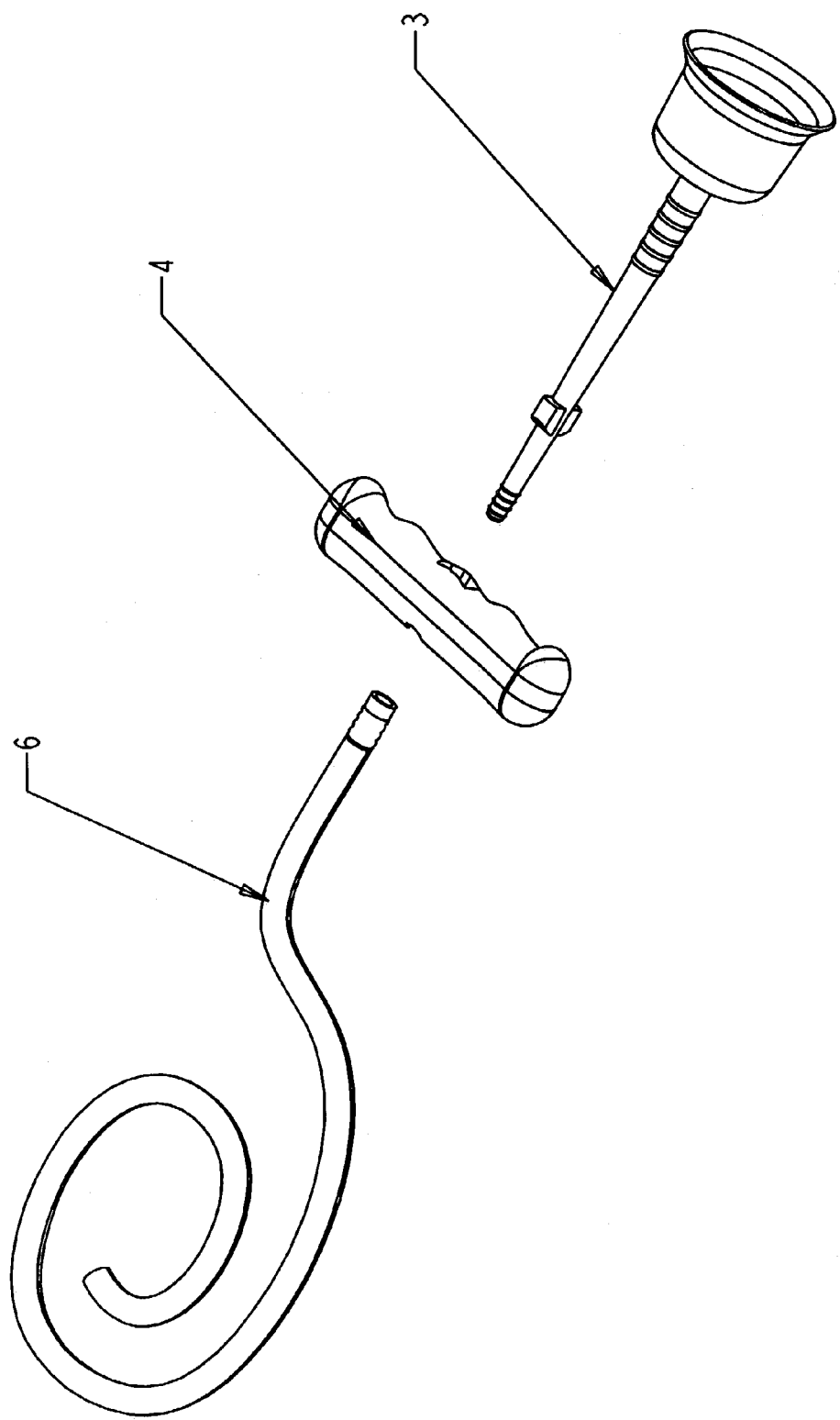

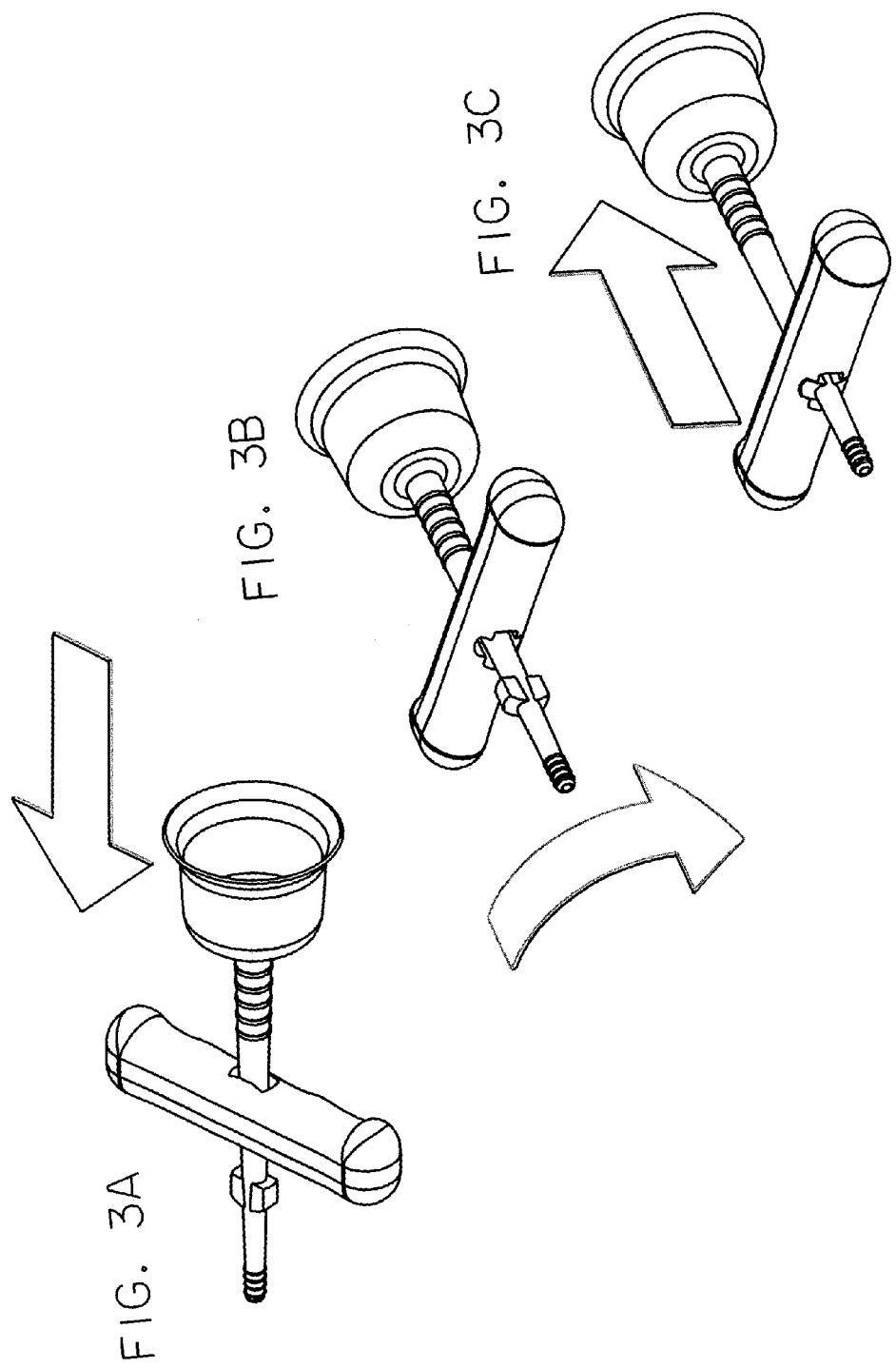

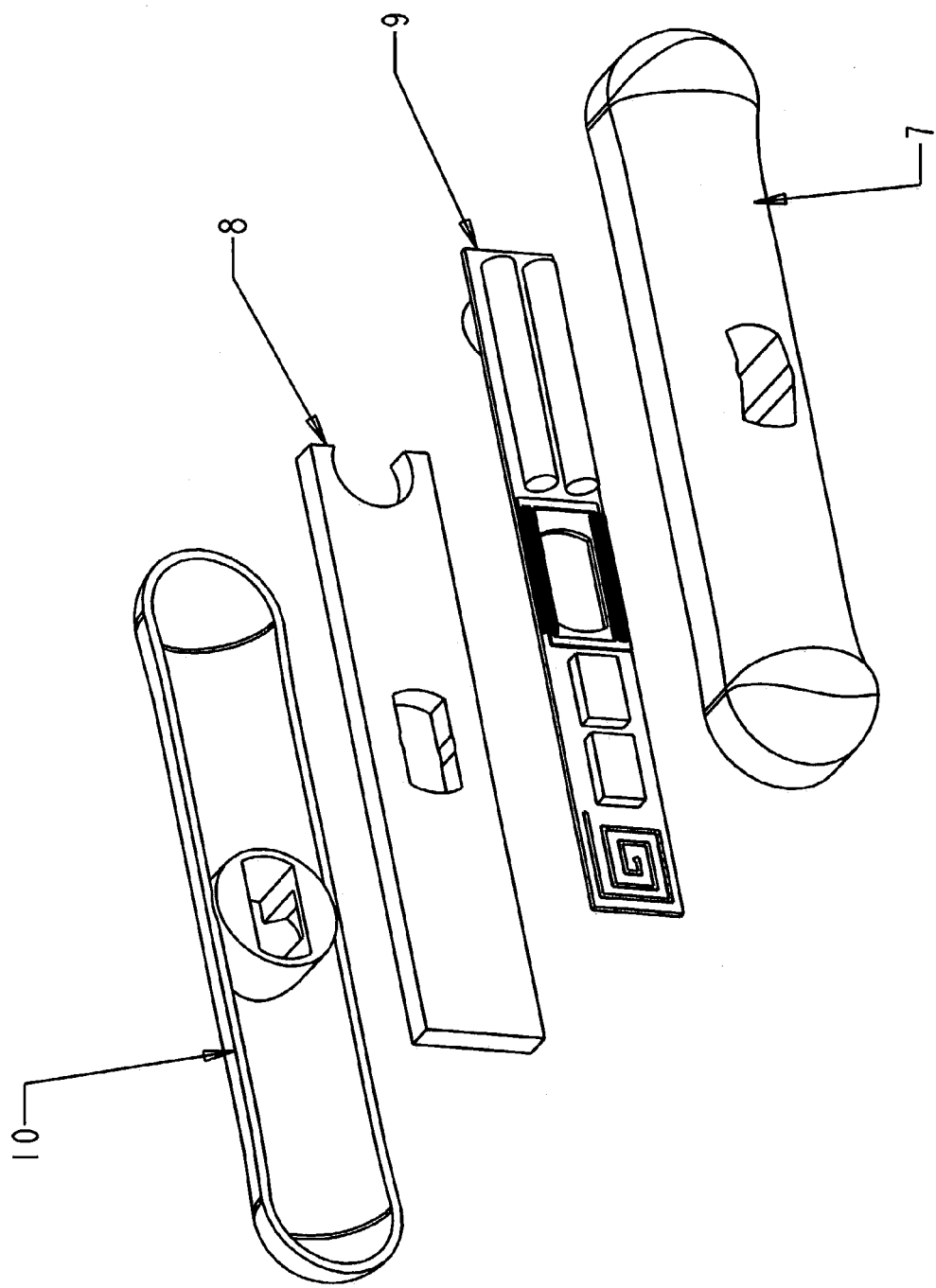

OBSTETRICAL VACUUM EXTRACTOR WITH A PULL-SENSING HANDLE GRIP

CROSS-REFERENCE TO RELATED APPLICATIONS

This application is a continuation-in-part of U.S. patent application Ser. No. 10/460,830, filed Jun. 12, 2003 now U.S. Pat. No. 7,163,544, which itself is a continuation-in-part of U.S. patent application Ser. No. 10/455,910, filed Jun. 6, 2003 now U.S. Pat. No. 7,014,642.

FIELD OF THE INVENTION

This invention pertains to devices for assisting in the delivery of a baby.

Specifically, the present invention relates to a new obstetrical vacuum extractor with a pull-sensing handle grip, containing electronic hardware whose purpose is to measure the traction force used during a delivery, to alert the doctor when the traction force approaches a level sufficient to cause cup detachment ("pop-off"), and to enable the wireless transmission of the traction data to a receiver connected to a lap-top computer with specific software, which generates a graphic representation of such data, and emits a warning signal when a pre-set time limit of continuous cup application on the fetal scalp is reached.

BACKGROUND OF THE INVENTION

The vacuum extractor is an obstetrical instrument, whose invention in 1849 is credited to Dr. James Young Simpson of Edinburgh (Scotland). It is comprised of a cup to be applied on the fetal head, of a tubing extending from the cup to a vacuum pump, and of a traction handle. As for the use of this instrument, once the cup is correctly applied to the fetal head (over the sagittal suture, with the posterior margin 3 cm forward of the posterior fontanelle, so that the center of the cup is over the flexion point of the fetal head), a vacuum pressure is generated under the cup with a hand pump or an electric pump. When the negative pressure within the cup reaches 550-600 mm Hg, traction is begun by pulling on the traction handle with the right hand perpendicular to the cup, while the left hand presses on the cup and the fetal head posteriorly, thus maintaining flexion of the head and the vector force follows the pelvic axis, which is the one of less resistance. Because the purpose of the vacuum is to augment the natural forces of labor, and not to replace them, traction is best applied in concomitance with the uterine contractions, for the so-called "push-pull effect."

The vacuum extractor is very valuable to shorten or to end the second stage of labor, whenever to do so is in the best interest of the mother or the fetus. Maternal indications for the use of the vacuum extractor include medical problems that would make the patient a poor candidate for a cesarean section, such as disabling cardio-pulmonary disease (mitral stenosis, congestive heart failure) or conditions that would worsen with excessive pushing, such as retinal detachment, or simple exhaustion from prolonged labor or protracted expulsive efforts. Fetal indications include conditions that expose the fetus to imminent danger of death, such as prolapse of the umbilical cord, bleeding from vasa previa, premature placenta separation, or a worrisome fetal heart pattern, and an emergency cesarean section cannot be done in a timely fashion.

The vacuum extractor requires less dexterity and thus, it is perceived as having greater safety, due to the decrease in compressive force, when compared to forceps. This may help explain why its use has increased from 3.5% to 5.9% of all deliveries from 1989 to 1995. However, the vacuum extractor is known to cause numerous fetal injuries, including scalp abrasive and ecchymotic lesions, and the more severe cephalohematomas (i.e., separation of the scalp from the underlying structures), subaponeurotic (a.k.a. subgalean) hemorrhage (i.e., collection of blood in the potential space between the cranial periosteum and the epicranial aponeurosis), intracranial hemorrhage (subdural, subarachnoid, intraventricular, and/or intraparenchimal), and retinal hemorrhage.

The incidence of the above fetal injuries can be reduced by limiting the negative pressure under the cup to 550-600 mm Hg, by keeping the cup on the fetal scalp for no longer than 15 minutes, and by avoiding cup "pop-offs." However, whereas the vacuum pressure and the time of cup application can be objectively determined, how to avoid cup "pop-offs" is left to the judgment of the obstetrician, who must learn from experience how much traction can be exerted before they happen. Consequently, detachment of the cup is very common, particularly in the hands of the novice, due to the general tendency to inadvertently apply a traction force that exceeds the adhesive force of the cup. Unfortunately, cup "pop-offs" expose the fetus not just to scalp abrasive and ecchymotic lesions, but potentially to the more severe injuries mentioned above, given the tendency in such instances to increase the negative pressure under the cup, in order to be able to apply a greater traction force.

Studies have been conducted to determine the detachment force, i.e., the maximum traction that the obstetrician can apply during a vacuum-assisted delivery without causing a cup "pop-off." Unfortunately, the instruments used to determine the detachment force of the various cups, while useful for research purposes, are not well suited for routine clinical use. Examples of such devices include those briefly described in the scientific literature by Moolgaoker A. S., et al., Mishell D., et al., Duchon M. A., et al, and Hofmeyr G. J., et al.

To the applicant's knowledge, the only vacuum extractor device presently in clinical use, in this country, with the means to measure the traction force, is the Kiwi vacuum delivery device (Clinical Innovations Inc., Murray, Utah 84123). However, this instrument has two serious drawbacks. The first is that the traction force during the vacuum-assisted delivery is measured through a mechanical gauge, and thus of limited precision. The second drawback is that in order to control the traction force that is being exerted on the fetal scalp, the doctor must divert the attention from the fetal contact cup to the small scale on the traction force indicator.

Accordingly, there is a need for an improved obstetrical vacuum extractor that can measure the traction forces applied to the fetal head without the constraints and design drawbacks seen in the prior art and described above.

SUMMARY OF THE INVENTION

The invention consists of a new obstetrical vacuum extractor which includes a bell-shaped fetal contact cup, made of flexible material, with a hollow and substantially rigid stem, a pull-sensing handle grip attached to the end of the stem, and a tube connected with one end to the cup stem and with the other to a vacuum source. The pull-sensing handle grip contains electronic hardware whose purpose is to reduce the risk of fetal trauma caused by frequent cup detachment ("pop-off") and excessive traction force, during a vacuum-assisted delivery. The hardware includes a strain gauge to measure the traction force applied to the vacuum extractor during a delivery, a speaker to alert the doctor when the traction force approaches a level sufficient to cause a fetal cup "pop-off," and a transceiver for the wireless transmission of the traction data to a receiver connected to a lap-top computer, which generates a graphic representation of such data, and emits a warning signal when a pre-set time limit of continuous cup application on the fetal scalp is reached.

A novel feature of this invention is the measurement of the traction force exerted on the fetal scalp during a vacuum-assisted delivery through electronic hardware, which is more precise than mechanical gauges. Another novel feature of this invention is that the doctor will be automatically alerted through a speaker contained in the handle, when the traction force approaches a level sufficient to cause a fetal cup "pop-off." Another novel feature of this invention is the wireless transmission of the traction data throughout the vacuum-assisted delivery to a receiver connected with a lap-top computer, eliminating the need for cumbersome cable connections. A further novel feature of this invention is the graphic representation in real-time, of the traction force exerted on the fetal head during the vacuum-assisted delivery, useful for research purposes or in case of medical malpractice litigation. A still further novel feature of this invention is that the obstetrician will be automatically reminded through a timer in the lap-top computer, of the pre-set time limit of continuous cup application on the fetal head and thus, of the need to abandon the vacuum procedure. A still further novel feature of this invention is that the electronic handle assembly can be either disposed after a single use, or it can be easily re-sterilized, without significant impact on materials or functionality. An additional novel feature of this invention is the easy adaptability of the pull-sensing handle to any fetal contact cup shape, not just to the bell-shaped cup shown in the drawings.

The foregoing has outlined rather broadly the features and technical advantages of the present invention so that the detailed description of the invention that follows may be better understood. Additional features and advantages of the invention will be described hereinafter, which form the subject of the invention. It should be appreciated by those skilled in the art that the conception and the specific embodiment disclosed might be readily used as a basis for modifying or designing other obstetrical vacuum extractors with a pull-sensing handle grip for carrying the same purposes of the present invention. It should also be realized by those skilled in the art that such equivalent constructions do not depart from the spirit and scope of the invention as set forth herein.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings:

FIG. 2 is an exploded view of the obstetrical vacuum extractor with a pull-sensing handle grip, a fetal contact cup with its stem, and the vacuum tubing;

FIGS. 3A, 3B, and 3C illustrate how the cup stem and the pull-sensing handle grip are assembled;

FIG. 4 represents an exploded view of the pull-sensing handle grip with a structural bridge, a printed circuit board assembly, and a top and bottom of the grip housing.

It is to be noted that the drawings illustrate only typical embodiments of the invention and are therefore not to be considered limiting of its scope, for the invention will admit to other equally effective embodiments.

DETAILED DESCRIPTION OF THE INVENTION

The present invention obviates the problems of the prior art by providing a new vacuum extractor, with a pull-sensing handle grip containing electronic hardware, which can measure the traction force exerted on the fetal scalp with greater precision. In addition, it automatically alerts the doctor when such a force approaches a level sufficient to cause the fetal cup to "pop-off." Furthermore, a transceiver contained in the handle allows the wireless transmission of the traction data to a receiver connected to a lap-top computer, which generates a graphic representation of such data, and emits a warning signal when a pre-set time limit of continuous cup application on the fetal scalp is reached.

Figure 1:
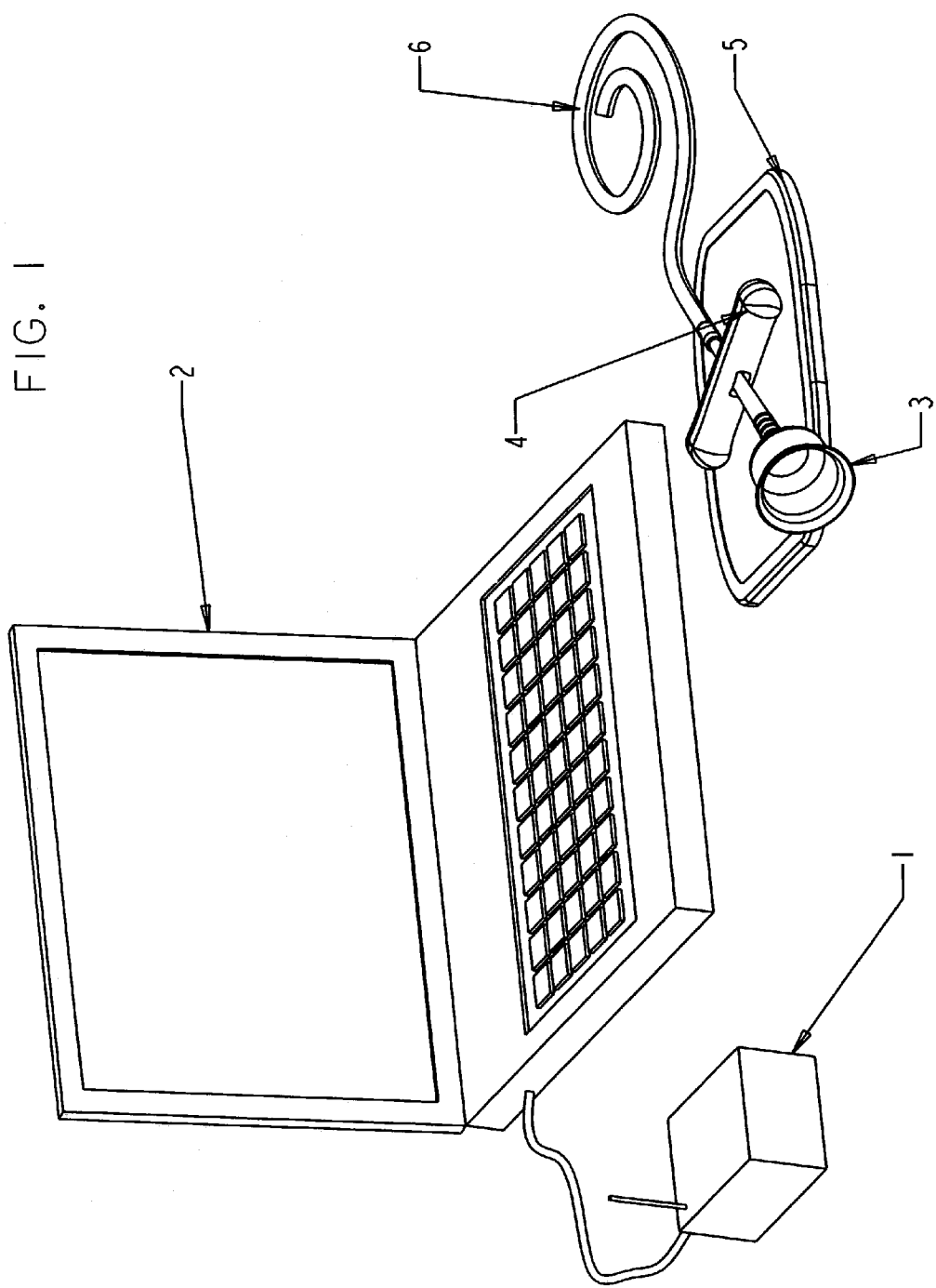
FIG. 1 shows an obstetrical vacuum extractor assembled with a pull-sensing handle grip resting on a recharge pad, and a radio receiver connected to a lap-top computer.

Turning now to FIG. 1, there is shown the new obstetrical vacuum extractor with a bell-shaped fetal contact cup made of flexible material with a substantially rigid and hollow stem, a pull-sensing handle grip attached to the end of the stem, and a tube connected with one end to the cup stem and with the other to a vacuum source (not shown). The handle grip assembly (4) rests on a recharging pad (5) used to inductively recharge the power supply or batteries housed within the handle grip assembly (4).

As also seen in FIG. 1, a radio receiver (1) is connected with a lap-top computer (2), which displays and records the pull data transmitted by the handle grip assembly and generates a graphic recording of said data, which can be stored, analyzed, processed, or otherwise made part of the patient's hospital medical record. In addition, the lap-top computer will remind the obstetrician through a timer, of a pre-set time limit of continuous cup application on the fetal head, typically 15 minutes, and thus of the need to abandon the vacuum procedure.

While many different types of vacuum extractors have been described and developed throughout time, they consist principally of the following three major components:

A) the cup—(3): the cup can be either rigid or soft. The rigid cup is mushroom-shaped, made of metal, and comes in various sizes (40, 50, and 60 mm in diameter). The soft cups, which in this country are preferred to the rigid ones, are funnel or bell-shaped, made of pliable silicone or plastic materials, and are each of one size. In addition, the soft cups have an elongated, hollow stem with an opening through which a vacuum may be provided within the cup itself.

B) the traction handle—(4): the traction handle is where the doctor holds the vacuum extractor and applies traction to the fetal head.

C) the vacuum tubing—(6): the tubing is connected with one end to the cup and with the other to a hand pump or an electric pump, to generate vacuum pressure under the cup.

FIG. 2 shows the three components of the present invention: the fetal contact cup (3) with its stem (18) with tang (19) and barb (20), the pull-sensing handle grip (4), and the vacuum tubing (6).

Turning now to FIGS. 3A, 3B, and 3C, there is shown how the cup stem and the pull-sensing handle come together. In particular, the stem (18) of the cup has a tang (19) which is lined up with the rectangular opening (21) on the grip housing top and inserted all the way through the handle, coming out of the grip housing bottom. The cup is then rotated 90 degrees in either direction, and pulled back out until it clicks into place within a recess. The vacuum tubing (not shown) is then inserted over the cup stem barb (20) and the vacuum extractor is ready to use.

FIG. 4 shows that the pull-sensing handle grip is made of a top (7) and bottom (10) snap-on plastic housing. The top plastic housing is provided with a rectangular opening (21) and with the usual contoured finger-gripping surface for facilitating gripping by hand. The pull-sensing handle grip houses a structural bridge (8), which is the structural base for the printed circuit board (PCB) assembly (9), whose purpose is to measure the traction force applied during a delivery, to transmit data, and to control the power envelope.

Figure 5A:
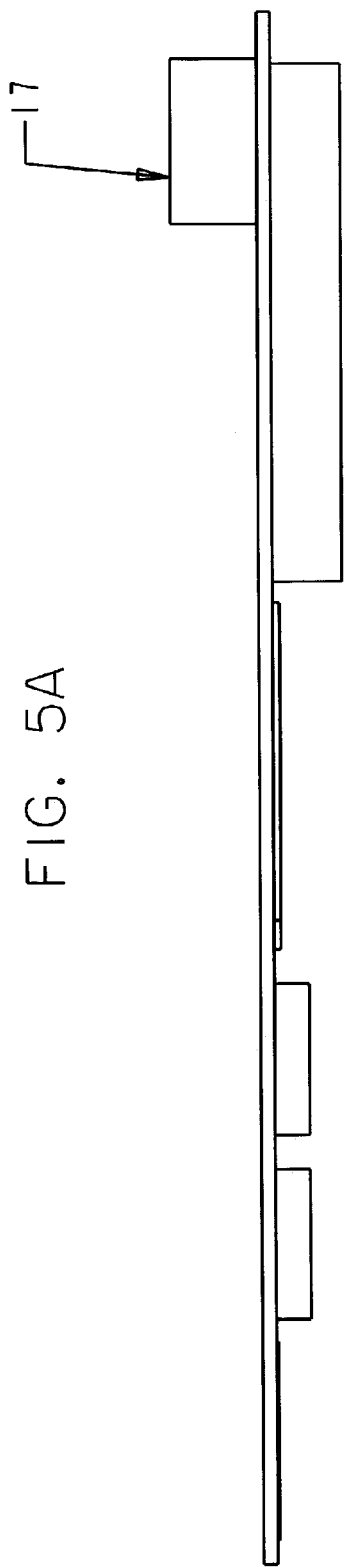
FIGS. 5A and 5B illustrate the side and top view of the printed circuit board with a radio frequency antenna, a transceiver chip, a microprocessor chip, a field coil recharger, a strain gauge, a re-chargeable battery, and a speaker.
Figure 5B:
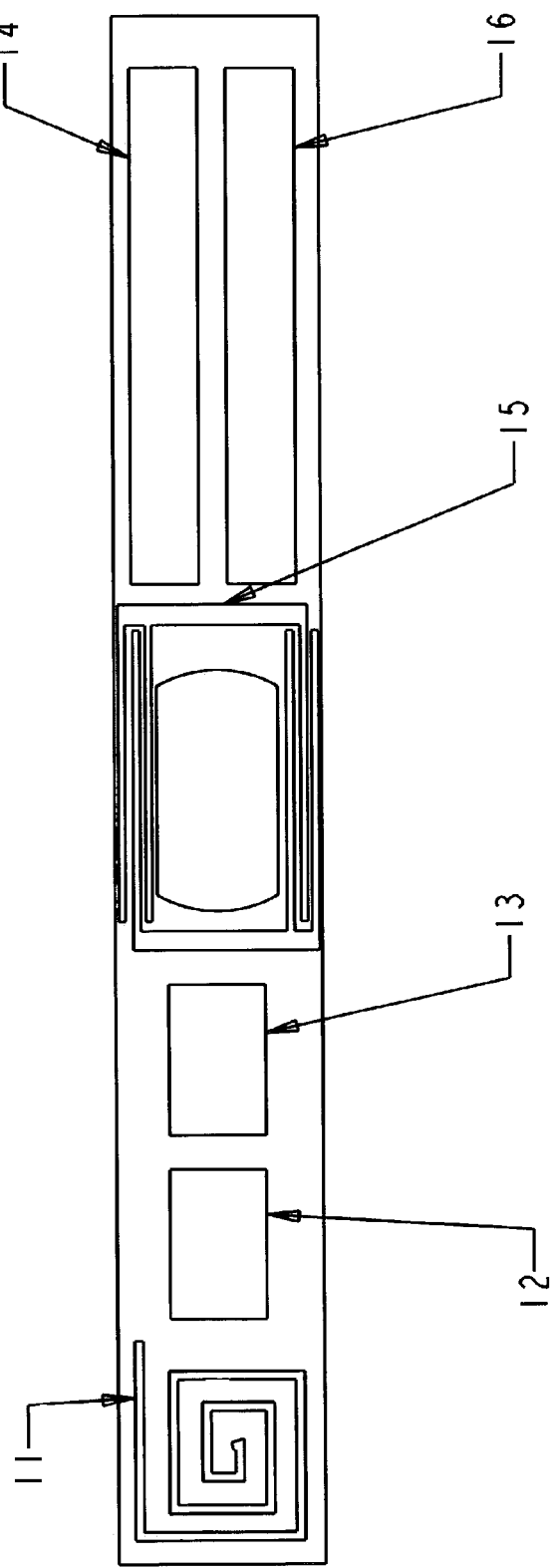

As seen in FIGS. 5A and 5B, the PCB assembly consists of a strain gauge (15), which measures the traction force between the grip assembly and the vacuum cup, a microprocessor chip (13), which controls the functions of the grip assembly, a transceiver chip (12), which controls radio communications between the grip assembly and the radio receiver (1), a rechargeable battery (16), which provides power during the use of the vacuum extractor, a field coil recharger (14), which provides recharging power to the battery when the pull-sensing handle grip rests on the recharging pad (5), a speaker (17), which creates an audible warning alarm when a preset traction force limit has been reached, and a radio frequency antenna (11), which relays data between the handle grip assembly and the receiver.

As seen in FIG. 1, the radio receiver (1) is connected with a lap-top computer (2), which records the traction data transmitted by the grip assembly and generates a graphic recording, which can be made part of the patient's hospital medical record. In addition, the lap-top computer has a timer which can be initialized by an assistant as the vacuum cup is applied by the obstetrician on the fetal head, so that a warning signal will be emitted when the 15-minute time limit of continuous cup application is reached, reminding the doctor to desist from further extractive efforts.

In addition, as for the sterilization of the instrument, the new obstetrical vacuum extractor with the pull-sensing handle grip can be provided already assembled in individually pre-packed sterile pouches and disposed after a single use. On the other hand, the pull-sensing grip can be re-sterilized and reused without any damage to the electronic hardware. In such a case, the handle is provided in one sterile pouch and the cup and the vacuum tubing in another, with the latter disposed after a single use. Sterilization of the handle can be accomplished either through a low temperature sterilization process (such as the STIRRAD method), or, alternatively, by immersion in a sterilizing solution (such as CIDEX). In fact, the printed circuit board is encapsulated within the plastic grip with epoxy compound, thus it is impervious to immersion in a liquid disinfectant.

Although the present invention and its advantages have been described in detail, it should be understood that various changes, substitutions, and alterations could be made herein without departing from the spirit and scope of the invention as defined by the appended claims.

What is claimed is:

1. An apparatus for the delivery of a fetus comprising:
   an obstetrical vacuum extractor with a pull-sensing handle grip, said grip comprising means for measuring electronically the magnitude of the extraction force applied to the fetal head during a vacuum extraction.

2. The apparatus of claim 1 wherein said means for measuring electronically the magnitude of the extraction force is a strain gauge.

3. The apparatus of claim 1 further comprising:
   means for producing an alarm when the extraction force exceeds a predetermined level.

4. The apparatus of claim 3 wherein said means for producing an alarm is a speaker.

5. An apparatus for the delivery of a fetus comprising:
   a bell-shaped vacuum cup;
   a hollow, substantially rigid stem extending from said cup, said stem having a tang on the opposite end;
   a handle grip that is detachable from the end of the stem, said handle having an opening through which said tang is inserted;
   means for measuring the extraction forces exerted on the fetal head, said means contained in said handle grip; and means for transmitting said extraction forces.

6. The apparatus of claim 5 further comprising:
   means for receiving said extraction forces.

7. The apparatus of claim 6 wherein said means for receiving said extraction forces is a wireless receiver.

8. The apparatus of claim 5 further comprising:
   means for the graphic representation of said extraction forces.

9. The apparatus of claim 8 wherein said means for the graphic representation of the extraction forces is a lap top computer with specific software.

10. The apparatus of claim 5 further comprising:
    means for the emission of a warning signal when a pre-set time limit of continuous cup application is reached.

11. The apparatus of claim 10 wherein said means for the emission of warning signal when a pre-set time limit of continuous cup application is reached is a lap top computer with a timer.

12. The apparatus of claim 5 wherein said means for measuring the extraction forces exerted on the fetal head is a strain gauge.

13. The apparatus of claim 5 wherein said means for transmitting said extraction forces is a wireless transmitter.

14. The apparatus of claim 5 further comprising:
    means for producing an alarm when said extraction forces exceed a predetermined level.

15. The apparatus of claim 14 wherein said means for producing an alarm is a speaker.

16. The apparatus of claim 15 wherein said speaker is contained in said handle grip.

17. Ah apparatus for the delivery of a fetus comprising:
    a bell-shaped vacuum cup made of flexible material;
    a hollow, substantially rigid stem, extending from the cup and with a tang on the opposite end, which fits in the opening of the grip housing top;
    a handle grip that is detachable from the end of the stem, said handle grip comprising
    means for measuring the extraction forces on the fetal head, and
    means for transmitting said extraction forces;
    means for receiving said extraction forces;
    means for the graphic representation of said extraction forces;
    means for the emission of a warning signal when a pre-set time limit of continuous cup application is reached; and
    a tubing connected with one end to the stem and with the other to a vacuum source.

18. The apparatus of claim 17 wherein said handle grip further comprises means for producing an alarm when the extraction force exceeds a predetermined level.

* * * * *